(12) United States Patent
Feng et al.

(10) Patent No.: US 11,609,195 B2
(45) Date of Patent: Mar. 21, 2023

(54) EXPERIMENTAL METHOD OF TYPE I STRESS INTENSITY FACTOR TEST CONSIDERING PERIODIC CHANGES OF FROST-HEAVE FORCES

(71) Applicant: Shandong University of Science and Technology, Shandong (CN)

(72) Inventors: Qiang Feng, Shandong (CN); Zedong Yang, Shandong (CN); Shuang Zhang, Shandong (CN); Jichao Jin, Shandong (CN); Weiwei Liu, Shandong (CN); Zhe Qin, Shandong (CN); Tingchun Li, Shandong (CN)

(73) Assignee: Shandong University of Science and Technology, Shandong (CN)

( * ) Notice: Subject to any disclaimer, the term of this patent is extended or adjusted under 35 U.S.C. 154(b) by 0 days.

(21) Appl. No.: 17/794,387

(22) PCT Filed: Apr. 21, 2021

(86) PCT No.: PCT/CN2021/088698
§ 371 (c)(1),
(2) Date: Jul. 21, 2022

(87) PCT Pub. No.: WO2021/258833
PCT Pub. Date: Dec. 30, 2021

(65) Prior Publication Data
US 2022/0381715 A1 Dec. 1, 2022

(30) Foreign Application Priority Data

Jun. 24, 2020 (CN) .......................... 202010590498.7

(51) Int. Cl.
*G01N 25/14* (2006.01)
*G01N 3/60* (2006.01)
(Continued)

(52) U.S. Cl.
CPC .......... *G01N 25/14* (2013.01); *G01M 99/002* (2013.01); *G01N 1/286* (2013.01); *G01N 3/60* (2013.01); *G01N 17/002* (2013.01)

(58) Field of Classification Search
CPC ........ G01N 25/14; G01N 3/60; G01N 17/002; G01M 99/002
See application file for complete search history.

(56) References Cited

FOREIGN PATENT DOCUMENTS

| CN | 107064288 A | 8/2017 |
|---|---|---|
| CN | 108613890 A | 10/2018 |

(Continued)

OTHER PUBLICATIONS

English translation of International Search Report for Application PCT/CN2021/088698 dated Jul. 23, 2021.

(Continued)

*Primary Examiner* — Paul M. West
(74) *Attorney, Agent, or Firm* — McClure, Qualey & Rodack, LLP

(57) ABSTRACT

An experimentation method for a type I stress intensity factor test considering frost heaving force periodic changes, steps being 1: preparing a specimen, waterjet cutting on the specimen to simulate a non-penetrating rock mass fracture; step 2: vacuum saturating the specimen; step 3: affixing a strain gauge in a non-elastic area at a tip of the specimen; step 4: placing the specimen into a rock mass (1) fracture frost heaving experiment box (5), pressurizing by a pressurizing apparatus (4) balloons on either side of the frost heaving experiment box (5), shutting a valve and removing a pipe, placing the frost heaving experiment box (5) holding the specimen into a water tank, allowing water to immerse the specimen; and step 5: placing the water tank and the frost heaving experiment box (5) holding the specimen together (Continued)

into a high-low temperature alternating experiment box (7) to start a freeze-thaw cycle experiment.

3 Claims, 2 Drawing Sheets

(51) Int. Cl.
    *G01N 17/00*      (2006.01)
    *G01M 99/00*      (2011.01)
    *G01N 1/28*      (2006.01)

(56)      References Cited

FOREIGN PATENT DOCUMENTS

| | | |
|---|---|---|
| CN | 108982205 A | 12/2018 |
| CN | 110940693 A | 3/2020 |
| CN | 111721800 A | 9/2020 |
| JP | 5695554 B2 | 4/2015 |

OTHER PUBLICATIONS

English translation of Written Opinion accompanying International Search Report in PCT/CN2021/088698 dated Jul. 23, 2021.

EXPERIMENTAL METHOD OF TYPE I STRESS INTENSITY FACTOR TEST CONSIDERING PERIODIC CHANGES OF FROST-HEAVE FORCES

TECHNICAL FIELD

The present invention relates to the technical field of civil engineering, especially an experimental method of type I stress intensity factor test considering periodic changes of frost-heave forces.

BACKGROUND TECHNOLOGY

Upon excavation disturbance of tunnels enclosing rocks will deform and crack, in aqueous and freeze-thaw cyclic conditions, rock matrixes and the cracks are liable to be damaged, and researches on features of the damages and evolution rules thereof are a basic problem for tunnels in cold regions. Many scholars test physical and dynamic properties of the rocks after freeze-thaw cycles by experiments and have obtained abundant products, and it is established that freeze-thaw acts on the rocks by promoting weathering thereof and deteriorates physical and dynamic properties thereof. Researches showed that freeze-thaw cycle actions can result in damages of the rocks and deterioration of physical and dynamic properties thereof and the changing trend has been commonly recognized.

After making clear that freeze-thaw actions can damage the rocks, it remains a focus of researchers as to how to characterize quantitatively and describe accurately the evolution rules. However, currently, results of characterization of freeze-thaw damages of the rock masses and the cracks are not accurate enough.

SUMMARY OF INVENTION

A purpose of the present invention is to address deficiencies of the prior art as described in the foregoing paragraphs, and provide an experimental method of type I stress intensity factor test considering periodic changes of frost-heave forces, simulate freeze-thaw status of rock masses with intermittent cracks realistically, and represent accurately freeze-thaw damage results of cracked rock masses.

An experimental method of type I stress intensity factor considering periodic changes of frost-heave forces, comprising following steps:

Step 1: making a testing piece, cutting with a waterjet cutter a seam on three surfaces of the testing piece to imitate a crack on a rock mass with an intermittent crack;

Step 2: vacuuming and saturating the testing piece;

Step 3: pasting strain foils with distances of respectively r1 and r2 at a range of a non-plastic area at a sharp end of a y-axis;

Step 4: putting the testing piece into a rock crack freeze-thaw testing box, pressurizing with a pressurizing device air bags at both sides of the freeze-thaw testing box and filling liquid into the air bags, closing the crack at two surfaces of the testing piece with the air bags, closing the crack at another surface of the testing piece by pasting at least one rubber sheet, after closing the crack in the testing piece, and putting the freeze-thaw testing box containing the testing piece into a water tank, and immersing the testing piece in water;

Step 5: putting the water tank and the freeze-thaw testing box containing the testing piece into a high and low temperature experiment box for freeze-thaw experiments; and Step 6: obtaining values and positions of the two strain foils on the y-axis based on rock mass crack freeze-thaw experiments, and calculating the type I stress intensity factor Km caused by frost-heave forces by a formula (1);

Establishing a mathematical expression between the stress intensity factor Km and a number of cycles depending on the values of the strain foils in different cycles, and obtaining the type I stress intensity factor considering periodic changes of frost-heave forces;

$$K_{1-1} = \frac{4\sqrt{\pi}(\varepsilon_1 \sqrt{r_1} \, r_2 - \varepsilon_2 r_1 \sqrt{r_2})}{E(\mu - 3)(r_1 - r_2)} \quad (1)$$

In the formula: E and µ are respectively elastic modulus and Poisson's ratio, $\varepsilon_1$ and $\varepsilon_2$ are respectively strain values measured at radius $r_1$ and $r_2$.

Preferably, the liquid pressurized in the air bags is glycol water solution.

Preferably, a size of the testing piece is 200 mm×100 mm×100 mm.

The present invention has the following beneficial effects:

In the present invention, by adding water in a crack of the testing piece efficiently without allowing water to flow out, and closing the crack in the testing piece during freezing, freeze-thaw status of a rock mass with intermittent cracks has been imitated realistically, so that freezing damage results of cracked rock masses can be represented accurately.

Figure 4:
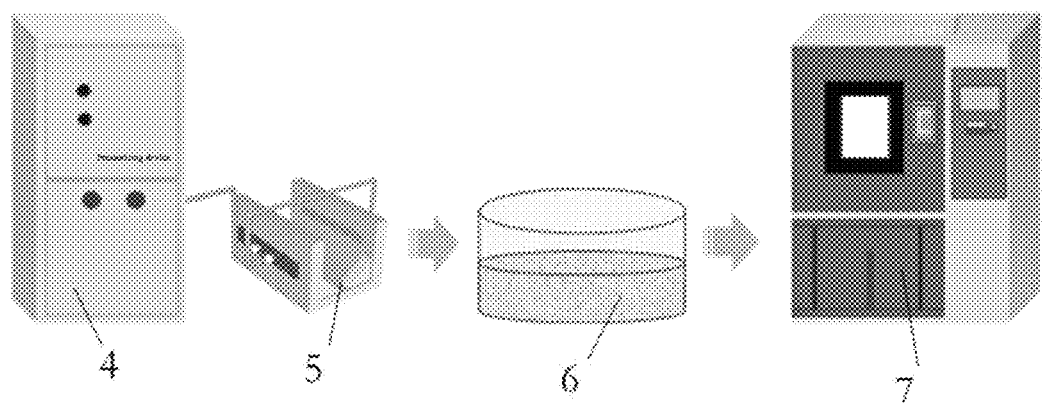

Wherein, area I is a plastic area; area II is a flexible area; III area is a far field area; r1 and r2 correspond respectively to strain foils;

FIG. 4 is a flowchart diagram showing freeze-thaw cycle test of a cracked test piece;

In the drawings: 1—rock; 2—water passage hole; 3—rubber sack; 4—pressurizing device; 5—crack freeze-thaw test box; 6—water tank; and 7—high and low temperature experiment box.

EMBODIMENTS

To make purposes, technical solutions and advantages of the present invention clearer, hereinafter the technical solutions of the present invention will be described clearly and completely, obviously, the embodiments given here are only some embodiments of the present invention rather than all. Based on the embodiments of the present invention, all other embodiments obtained by those of ordinary skill in the art without involving creative effort shall fall within the protection scope of the present invention.

Figure 1:
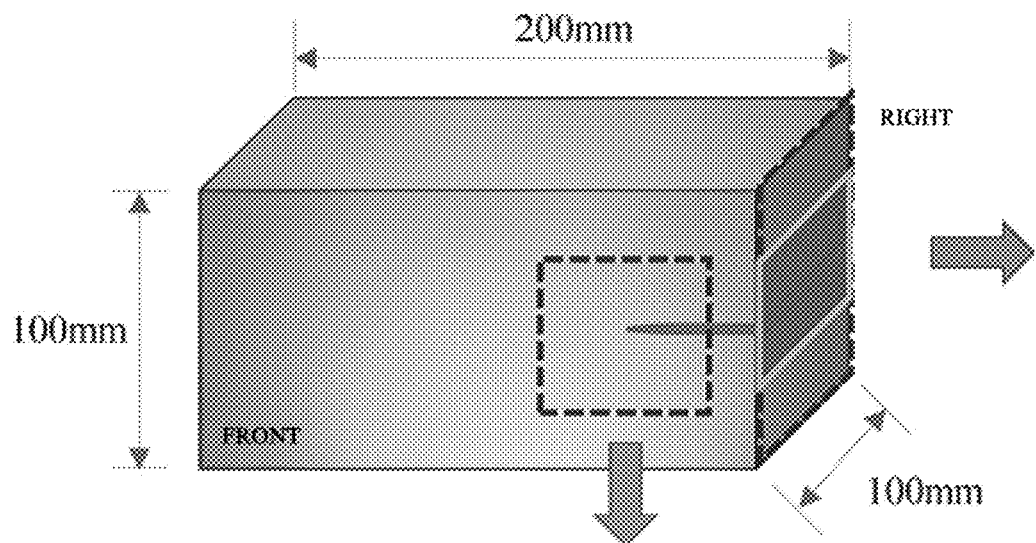
FIG. 1 is a perspective view of the freeze-thaw cycle testing piece.
Figure 2:
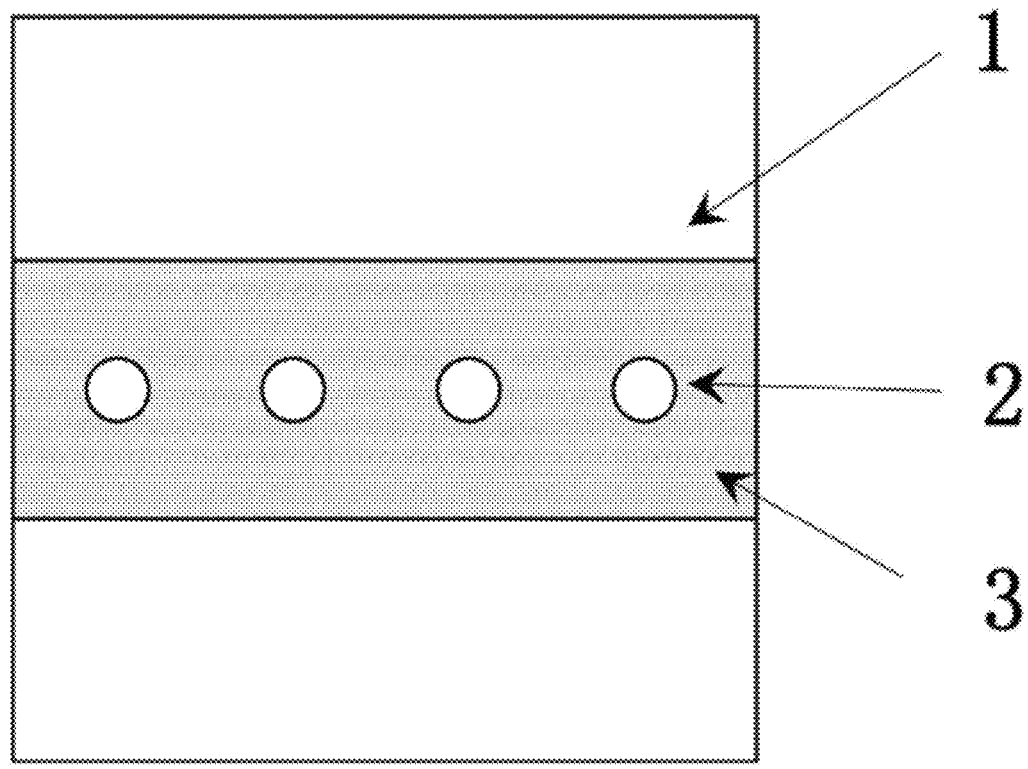
FIG. 2 is a right side view of FIG. 1.
Figure 3:
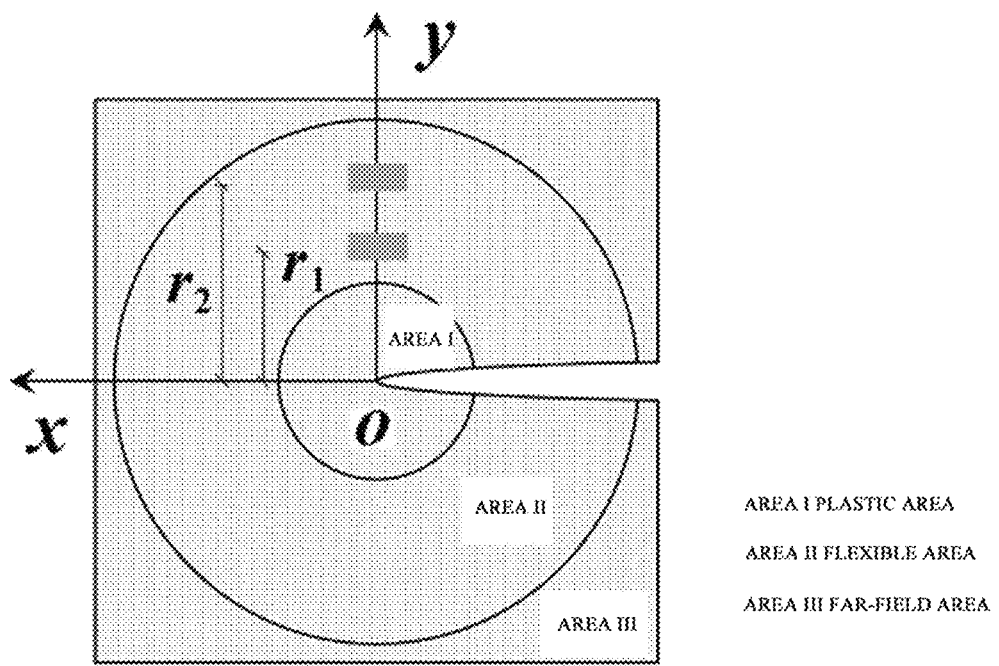
FIG. 3 is a front view of FIG. 1.

As shown in FIG. 1 to FIG. 3, make a testing piece with a size of 200 mm×100 mm×100 mm (length×width×height), as the cracks open when subjected to frost-heave forces, seams cut by a waterjet cutter can be used to simulate the cracks, as shown in FIG. 1. Vacuum and saturate the testing piece, determine a radius $r_p$ (area I) of a plastic area by numerical simulation; paste strain foils with distances of respectively $r_1$ and $r_2$ at a range of an area II at a y-axis ($r_1/r_p \geq 4$, $r_2/r_1 \approx 3$, $r_2 - r_1 \geq 4$), stick a rubber sheet at a lower side and an upper side of the crack with glue at a right side (reserve allowance at the rubber sheet in an intermediate portion that is not glued, avoid encountering resistance when the crack opens and deforms when subjected to the frost-heave actions), and water passage holes for supplementing water to the crack during freeze-thaw cycles are reserved at the rubber sheet that is not covered with glue.

As shown in FIG. 4, after the glue is cured, put the testing piece into a self-made rock crack freeze-thaw experiment box, fill refrigerating fluid (containing primarily glycol water solution with a freezing point as low as −40° C.) into rubber sacks at side panels of the experiment box, in the meanwhile, stabilize the pressure to be 5 MPa, turn off a valve connected with the pressurizing device, and close openings of the crack at the front surface and the rear surface by expansion and deformation of the rubber sacks. Put the crack freeze-thaw test box and the testing piece into a water box filled with water, put all of them into a high and low temperature test box for freeze-thaw cycle experiments, set a number of cycles to be 0, 20, 40, 60 and 100, and test rules of changes of the strain near a sharp end of the crack along with freeze-thaw times.

Specifically, the operation method is:

Step 1: making a testing piece, cutting a crack with a waterjet cutter in the testing piece to simulate the crack in a rock mass with intermittent cracks;

Step 2: vacuuming and saturating the testing piece;

Step 3: pasting strain foils at a range of non-plastic areas at a sharp end of the testing piece;

Step 4: putting the testing piece into a rock crack freeze-thaw testing box, pressurizing air bags at both sides of the freeze-thaw test box with a pressurizing device, pressurizing glycol water solution into rubber sacks, turning off a valve, removing pipelines, putting the freeze-thaw test box containing the testing piece into a water tank and immersing the testing piece in water;

Step 5: putting auxiliary devices mentioned in step 4 into a high and low temperature experimental box, starting freeze-thaw cycle test, setting a number of cycles to be respectively 0, 20, 40, 60 and 100, and testing rules that the strain foils at a sharp end of the crack change along with times of freeze-thaw by measuring displacement of the strain foils;

Step 6: calculating the type I stress intensity factor $K_{i-1}$ caused by frost-heave forces by a formula (1) based on the rock crack freeze-thaw cycle tests and values and positions of the two strain foils at the y axis; establishing a mathematical expression between the stress intensity factor $K_{I-1}$ and a number of cycles depending on the values of the strain foils in different cycles, and obtaining the type I stress intensity factor considering periodic changes of frost-heave forces.

$$K_{1-1} = \frac{4\sqrt{\pi}\left(\varepsilon_1\sqrt{r_1}\,r_2 - \varepsilon_2 r_1 \sqrt{r_2}\right)}{E(\mu - 3)(r_1 - r_2)} \quad (1)$$

In the formula: E and μ stand for elastic modulus and Poisson' ratio in the current cycle. What influences the stress intensity factor in freeze-thaw conditions includes: (1) when subjected to coldness, water in cracks in a rock will produce frost-heave forces, which act on the cracks in the rock, and the cracks are cause to develop and be bigger; and (2) water in pores of the rock are frozen and thawed and frost-heave forces are generated, so the rock is damaged, and the ability of the rock to go against extension of the cracks is deteriorated. Finally, the stress intensity factor is caused to change, and in the step 2, the purpose of vacuum and saturate the rock is to have the pores in the rock saturated.

A method to prevent out flow of the water in the crack is:

The crack is open at three sides, two of which are closed by the rubber sacks in the experimental box, and the third side, that is, the right side is closed by sticking a rubber sheet. The way to close the crack: liquid is filled into the rubber sacks via a pressurizing device, as finally the rock is to be put into a temperature box, it shall be promised that the liquid in the rubber sacks won't freeze, and the liquid finally chosen is the above mentioned glycol water solution; the rubber sheet at the right side can close the crack if no water passage holes are opened thereon, however, as it is necessary to consider water refilling after thawing, so that water passage holes are provided, and as a direction that cold energy is transmitted is from outside in, ice clogging is liable to happen at the water passage holes, the problem that the water passage holes are not closed can be addressed. In this way, water in the crack will not flow out. Put the testing piece in the rock crack freeze-thaw testing box, let the rubber sacks corresponding to positions of the crack at a front side and a rear side of the testing piece at a left side and a right side of the testing box, by the rubber sacks the crack at the front side and the rear side of the testing piece can be closed; and the crack at the right side of the testing piece is closed with the rubber sheet; Pressurize freezing liquid into the rubber sacks at both side panels of the testing box with the pressurizing device, in the meanwhile, stabilize the pressure to be 5 MPa (the value is determined according to specific experiments), close a valve connected with the pressurizing device and close openings of the cracks at the front side and the rear side of the testing box by expansion and deformation of the rubber sacks.

A plurality of water passage holes are distributed on the rubber sheet, wherein positions of the plurality of water passage holes are distributed according to the position of the crack. In the meantime, put the rock crack freeze-thaw testing box into the water box;

Functions of the plurality of water passage holes are: first of all, during freezing, as the water passage holes are small, during transmission of the cold energy from outside in, ice clogging is liable to form at the water passage holes, so the crack can be closed at the right side; and secondly, during thawing, the water passage holes can be used to fill water into the crack.

Wherein, a method to freeze the liquid in the step 4 is: putting the same into the high and low temperature experimental box and freezing. Wherein, functions of the pressurizing device and the freeze-thaw testing box are to ensure that water can be successfully prevented from flowing out by the rubber sacks at the front side and the rear side.

The reason why glycol water solution is used in the rubber sacks is that during freezing the rubber sacks can serve the purpose of closing the water passage holes very well, so it is required there is liquid in the rubber sacks, and glycol water solution with a low freezing point is selected.

The purpose of putting the testing box into the high and low temperature experimental box is to freeze the water in the crack and the pores and thaw the water cyclically. The status when frozen is that the water in the water tank, the water in the crack and the water in the pores of the rock is frozen to be ice, while the glycol water solution in the rubber sacks is still in a liquid state Finally it shall be noted that: the foregoing embodiments are only used to explain the technical solutions of the present invention rather than limit them; although the present invention has been described in detail with reference to the foregoing embodiments, those of ordinary skill in the art shall appreciate that: it is still possible for them to modify the technical solutions recorded in the foregoing embodiments or replace some technical features therein with equivalent parts; and the modifications and replacements don't deviate the essence of the present invention from the spirit and scope of the technical solutions in the embodiments of the present invention.

The invention claimed is:

1. An experimental method of type I stress intensity factor considering periodic changes of frost-heave forces, comprising following steps:
   step 1: making a testing piece, cutting with a waterjet cutter a seam on three surfaces of the testing piece to imitate a crack on a rock mass with an intermittent crack;
   step 2: vacuuming and saturating the testing piece;
   step 3: pasting strain foils with distances of respectively r1 and r2 from an x-axis outside a plastic area at a sharp end of the test piece on a y-axis;
   step 4: putting the testing piece into a rock crack freeze-thaw testing box, pressurizing with a pressurizing device air bags at both sides of the freeze-thaw testing box and filling liquid into the air bags, closing the crack at two surfaces of the testing piece with the air bags, closing the crack at another surface of the testing piece by pasting at least one rubber sheet, after closing the crack in the testing piece, and putting the freeze-thaw testing box containing the testing piece into a water tank, and immersing the testing piece in water;
   step 5: putting the water tank and the freeze-thaw testing box containing the testing piece into a high and low temperature experiment box for freeze-thaw experiments; and
   step 6: obtaining values and positions of the two strain foils on the y-axis based on rock mass crack freeze-thaw experiments, and calculating the type I stress intensity factor k I-1 caused by frost-heave forces by a formula (1);
   establishing a mathematical expression between the stress intensity factor KI-1 and a number of cycles depending on the values of the strain foils in different cycles, and obtaining the type I stress intensity factor considering periodic changes of frost-heave forces;

$$K_{I-1} = \frac{4\sqrt{\pi}(\varepsilon_1 \sqrt{r_1} \, r_2 - \varepsilon_2 r_1 \sqrt{r_2})}{E(\mu - 3)(r_1 - r_2)} \quad (1)$$

in the formula: E and $\mu$ are respectively elastic modulus and Poisson's ratio, $\varepsilon_1$ and $\varepsilon_2$ are respectively strain values measured at radius $r_1$ and $r_2$.

2. The experimental method of type I stress intensity factor considering periodic changes of frost-heave forces according to claim 1, wherein the liquid pressurized in the air bags is glycol water solution.

3. The experimental method of type I stress intensity factor considering periodic changes of frost-heave forces according to claim 1, wherein a size of the testing piece is 200 mm×100 mm×100 mm.

* * * * *